(12) United States Patent
Murray et al.

(10) Patent No.: US 10,420,588 B2
(45) Date of Patent: Sep. 24, 2019

(54) ADJUSTING SPINAL CURVATURE

(71) Applicants: David Wycliffe Murray, Oxford (GB); James Wilson-Macdonald, Oxford (GB)

(72) Inventors: David Wycliffe Murray, Oxford (GB); James Wilson-Macdonald, Oxford (GB)

( * ) Notice: Subject to any disclaimer, the term of this patent is extended or adjusted under 35 U.S.C. 154(b) by 0 days.

(21) Appl. No.: 14/441,508

(22) PCT Filed: Oct. 16, 2013

(86) PCT No.: PCT/GB2013/052701
§ 371 (c)(1),
(2) Date: May 7, 2015

(87) PCT Pub. No.: WO2014/072680
PCT Pub. Date: May 15, 2014

(65) Prior Publication Data
US 2015/0289906 A1 Oct. 15, 2015

(30) Foreign Application Priority Data

Nov. 7, 2012 (GB) .................................. 1220042.4

(51) Int. Cl.
*A61B 17/70* (2006.01)
*A61B 17/84* (2006.01)
*A61B 17/86* (2006.01)

(52) U.S. Cl.
CPC ...... *A61B 17/7028* (2013.01); *A61B 17/7001* (2013.01); *A61B 17/7022* (2013.01);
(Continued)

(58) Field of Classification Search
CPC ............ A61B 17/7022; A61B 17/7001; A61B 17/8605; A61B 17/842; A61B 17/7007;
(Continued)

(56) References Cited

U.S. PATENT DOCUMENTS 3,693,616 A * 9/1972 Roaf .................. A61B 17/7049
606/250
4,078,559 A * 3/1978 Nissinen ............ A61B 17/7053
606/258
(Continued)

FOREIGN PATENT DOCUMENTS

FR 2799949 A1 4/2001
WO 9421185 A1 9/1994
(Continued)

OTHER PUBLICATIONS

International Search Report and Written Opinion to PCT/GB2013/052701 (13 pages).

*Primary Examiner* — Eduardo C Robert
*Assistant Examiner* — Michelle C Eckman
(74) *Attorney, Agent, or Firm* — Procopio, Cory, Hargreaves & Savitch LLP (57) ABSTRACT

Devices for adjusting or correcting the curvature of a vertebral column are described. One such device comprises a spring and at least three fixation members for attaching the spring to the vertebral column in at least three different locations. Another such device comprises a plurality of springs, each spring for attaching to at least two attachment locations of the vertebral column, and at least three fixation members for attaching the plurality of springs to the attachment locations of the vertebral column such that the plurality of springs are attached longitudinally along a length of the vertebral column. A method of adjusting the curvature of a vertebral column is also described.

12 Claims, 7 Drawing Sheets

(52) U.S. Cl.
CPC ........ *A61B 17/7029* (2013.01); *A61B 17/842* (2013.01); *A61B 17/8605* (2013.01)

(58) Field of Classification Search
CPC ............ A61B 17/7008; A61B 17/7019; A61B 17/7028–17/7029
USPC .......................................... 606/254–258, 263
See application file for complete search history.

(56) References Cited

U.S. PATENT DOCUMENTS

| | | | | |
|---|---|---|---|---|
| 4,274,401 A * | 6/1981 | Miskew | A61B 17/7004 | 606/256 |
| 4,815,453 A * | 3/1989 | Cotrel | A61B 17/7049 | 606/261 |
| 4,836,193 A * | 6/1989 | Ransford | A61B 17/7055 | 606/261 |
| 5,133,716 A * | 7/1992 | Plaza | A61B 17/7053 | 606/250 |
| 5,242,446 A * | 9/1993 | Steffee | A61B 17/7001 | 248/231.9 |
| 5,242,466 A * | 9/1993 | Aseervatham | D06M 11/38 | 8/543 |
| 5,290,289 A * | 3/1994 | Sanders | A61B 17/7002 | 606/151 |
| 5,658,286 A * | 8/1997 | Sava | A61B 17/7013 | 264/4 |
| 5,672,175 A * | 9/1997 | Martin | A61B 17/025 | 606/105 |
| 5,733,284 A * | 3/1998 | Martin | A61B 17/025 | 606/248 |
| 6,325,802 B1 * | 12/2001 | Frigg | A61B 17/7032 | 606/263 |
| 6,379,358 B1 * | 4/2002 | Kuo | A61B 17/7055 | 606/261 |
| 6,514,255 B1 * | 2/2003 | Ferree | A61B 17/7053 | 606/103 |
| 6,605,091 B1 * | 8/2003 | Iwanski | A61B 17/82 | 606/74 |
| 7,713,287 B2 * | 5/2010 | Timm | A61B 17/7028 | 606/257 |
| 7,717,941 B2 * | 5/2010 | Petit | A61B 17/7028 | 606/254 |
| 7,819,904 B2 * | 10/2010 | Golembiewski | A61B 17/56 | 606/246 |
| 8,317,830 B2 * | 11/2012 | Molz | A61B 17/7032 | 606/246 |
| 8,394,124 B2 * | 3/2013 | Biyani | A61B 17/7022 | 606/246 |
| 8,403,961 B2 * | 3/2013 | Fielding | A61B 17/7053 | 606/246 |
| 8,813,753 B2 * | 8/2014 | Bhat | A61B 5/0031 | 128/846 |
| 8,828,058 B2 * | 9/2014 | Elsebaie | A61B 17/7001 | 606/258 |
| 8,852,236 B2 * | 10/2014 | Kiester | A61B 17/70 | 606/258 |
| 9,011,499 B1 * | 4/2015 | Kiester | A61B 17/7016 | 606/246 |
| 2002/0143329 A1 * | 10/2002 | Serhan | A61B 17/0642 | 623/13.11 |
| 2003/0220643 A1 * | 11/2003 | Ferree | A61B 17/7023 | 623/17.16 |
| 2004/0049190 A1 * | 3/2004 | Biedermann | A61B 17/7008 | 606/257 |
| 2004/0106921 A1 * | 6/2004 | Cheung | A61B 17/7001 | 606/250 |
| 2004/0267260 A1 * | 12/2004 | Mack | A61B 17/7028 | 606/259 |
| 2005/0203511 A1 * | 9/2005 | Wilson-MacDonald | A61B 17/7044 | 606/254 |
| 2005/0209694 A1 * | 9/2005 | Loeb | A61B 17/7023 | 623/17.11 |
| 2005/0222569 A1 * | 10/2005 | Panjabi | A61B 17/7028 | 606/257 |
| 2005/0267470 A1 * | 12/2005 | McBride | A61B 17/7022 | 606/263 |
| 2006/0009767 A1 * | 1/2006 | Kiester | A61B 17/7016 | 606/258 |
| 2006/0064090 A1 * | 3/2006 | Park | A61B 17/7005 | 606/250 |
| 2006/0189985 A1 * | 8/2006 | Lewis | A61B 17/7007 | 606/257 |
| 2006/0195092 A1 * | 8/2006 | Barry | A61B 17/7077 | 606/86 A |
| 2006/0217726 A1 * | 9/2006 | Maxy | A61B 17/7062 | 606/248 |
| 2006/0247637 A1 * | 11/2006 | Colleran | A61B 17/7007 | 606/257 |
| 2006/0282073 A1 * | 12/2006 | Simanovsky | A61B 17/707 | 606/282 |
| 2007/0093822 A1 * | 4/2007 | Dutoit | A61B 17/68 | 606/258 |
| 2007/0123865 A1 * | 5/2007 | Schlapfer | A61B 17/701 | 606/257 |
| 2007/0233095 A1 * | 10/2007 | Schlaepfer | A61B 17/7031 | 606/279 |
| 2008/0033436 A1 * | 2/2008 | Song | A61B 17/7016 | 606/86 A |
| 2008/0051784 A1 * | 2/2008 | Gollogly | A61B 17/7014 | 606/279 |
| 2008/0140122 A1 * | 6/2008 | Bethell | A61B 17/70 | 606/263 |
| 2008/0140133 A1 * | 6/2008 | Allard | A61B 17/705 | 606/308 |
| 2008/0177319 A1 * | 7/2008 | Schwab | A61B 17/7014 | 606/257 |
| 2008/0177326 A1 * | 7/2008 | Thompson | A61B 17/7047 | 606/277 |
| 2008/0208256 A1 * | 8/2008 | Thramann | A61B 17/70 | 606/246 |
| 2008/0234747 A1 * | 9/2008 | Allard | A61B 17/7011 | 606/279 |
| 2008/0255615 A1 * | 10/2008 | Vittur | A61B 17/56 | 606/246 |
| 2008/0269805 A1 * | 10/2008 | Dekutoski | A61B 17/7004 | 606/279 |
| 2008/0275555 A1 * | 11/2008 | Makower | A61B 17/68 | 623/14.12 |
| 2008/0306536 A1 * | 12/2008 | Frigg | A61B 17/7002 | 606/246 |
| 2009/0030462 A1 * | 1/2009 | Buttermann | A61B 17/707 | 606/249 |
| 2009/0048631 A1 * | 2/2009 | Bhatnagar | A61B 17/7004 | 606/246 |
| 2009/0088803 A1 * | 4/2009 | Justis | A61B 17/7031 | 606/254 |
| 2009/0192548 A1 * | 7/2009 | Jeon | A61B 17/7011 | 606/246 |
| 2009/0248075 A1 * | 10/2009 | Ogilvie | A61B 17/7005 | 606/246 |
| 2009/0248088 A1 * | 10/2009 | Biedermann | A61B 17/7032 | 606/305 |
| 2009/0281575 A1 * | 11/2009 | Carls | A61B 17/70 | 606/278 |
| 2009/0326585 A1 * | 12/2009 | Baccelli | A61B 17/707 | 606/263 |
| 2010/0036424 A1 * | 2/2010 | Fielding | A61B 17/842 | 606/263 |
| 2010/0063548 A1 * | 3/2010 | Wang | A61B 17/7002 | 606/279 |
| 2010/0087872 A1 * | 4/2010 | Morihara | A61B 17/8861 | 606/300 |
| 2010/0249836 A1 * | 9/2010 | Seme | A61B 17/7001 | 606/246 |
| 2010/0249845 A1 * | 9/2010 | Meunier | A61B 17/7011 | 606/263 |

(56) References Cited

U.S. PATENT DOCUMENTS

| | | | |
|---|---|---|---|
| 2010/0249928 A1* | 9/2010 | Schwab | A61B 17/7019 623/13.14 |
| 2010/0262190 A1* | 10/2010 | Ballard | A61B 17/7005 606/264 |
| 2011/0004249 A1* | 1/2011 | Wu | A61B 17/701 606/254 |
| 2011/0066188 A1* | 3/2011 | Seme | A61B 17/7041 606/264 |
| 2011/0077687 A1* | 3/2011 | Thompson | A61B 17/7004 606/254 |
| 2011/0172708 A1* | 7/2011 | Fielding | A61B 17/7067 606/248 |
| 2011/0230914 A1 | 9/2011 | Engelmann et al. | |
| 2011/0245875 A1* | 10/2011 | Karim | A61B 17/7037 606/263 |
| 2011/0251643 A1* | 10/2011 | Miladi | A61B 17/7001 606/254 |
| 2011/0301645 A1* | 12/2011 | Connor | A61B 17/7016 606/263 |
| 2012/0101527 A1* | 4/2012 | Connor | A61B 17/7016 606/246 |
| 2012/0150231 A1* | 6/2012 | Alamin | A61B 17/1606 606/263 |
| 2012/0271354 A1* | 10/2012 | Baccelli | A61B 17/7053 606/263 |
| 2013/0090691 A1* | 4/2013 | Zhang | A61B 17/7001 606/264 |
| 2013/0150891 A1* | 6/2013 | Dodgen | A61B 17/7026 606/260 |
| 2013/0245701 A1* | 9/2013 | Kartalian | A61B 17/68 606/300 |
| 2013/0253587 A1* | 9/2013 | Carls | A61B 17/7022 606/263 |
| 2013/0345757 A1* | 12/2013 | Stad | A61B 17/7011 606/279 |
| 2014/0018807 A1* | 1/2014 | Foerster | A61B 17/82 606/74 |
| 2014/0094850 A1* | 4/2014 | Clement | A61B 17/7001 606/263 |
| 2014/0200615 A1* | 7/2014 | Yeh | A61B 17/7028 606/250 |
| 2014/0257396 A1* | 9/2014 | Powers | A61B 17/7022 606/259 |
| 2014/0277149 A1* | 9/2014 | Rooney | A61B 17/7053 606/263 |
| 2015/0080955 A1* | 3/2015 | Celmerowski | A61B 17/7005 606/254 |
| 2015/0164561 A1* | 6/2015 | Simpson | A61B 17/7002 606/264 |
| 2015/0201973 A1* | 7/2015 | Lindemann | A61B 17/7022 606/263 |
| 2015/0265316 A1* | 9/2015 | Schwab | A61B 17/7053 606/263 |
| 2015/0289906 A1* | 10/2015 | Murray | A61B 17/7001 606/263 |
| 2015/0305779 A1* | 10/2015 | Montavon | A61B 17/7001 606/257 |
| 2015/0313648 A1* | 11/2015 | Al Shail | A61B 17/7053 606/263 |
| 2015/0335363 A1* | 11/2015 | Walsh | A61B 17/707 606/249 |
| 2015/0342646 A1* | 12/2015 | Wessels | A61B 17/7053 606/255 |
| 2016/0008036 A1* | 1/2016 | Sachs | A61B 17/7041 606/258 |
| 2016/0038194 A1* | 2/2016 | Belliard | A61B 17/8869 606/263 |
| 2016/0051287 A1* | 2/2016 | Krause | A61F 2/44 606/255 |
| 2016/0106478 A1* | 4/2016 | Simpson | A61B 17/7053 606/263 |

FOREIGN PATENT DOCUMENTS

| | | | | |
|---|---|---|---|---|
| WO | 2005084567 A1 | 9/2005 | | |
| WO | WO 2013116150 A1 * | 8/2013 | | A61B 17/7032 |

* cited by examiner

ADJUSTING SPINAL CURVATURE

FIELD OF THE INVENTION

The invention relates to devices and methods for adjusting the curvature of a vertebral column, in particular a human vertebral column. The invention relates particularly, but not exclusively, to correcting curvature that may result from scoliosis.

BACKGROUND OF THE INVENTION

The vertebral column of a human being is typically made up of thirty-three vertebrae, which provide axial support to the trunk of the body and protection for the spinal cord. The majority of the vertebrae are articulated, and are separated by intervertebral disks that act as shock-absorbers. The remainder of the vertebrae are fused together, forming the sacrum and coccyx.

Figure 1:
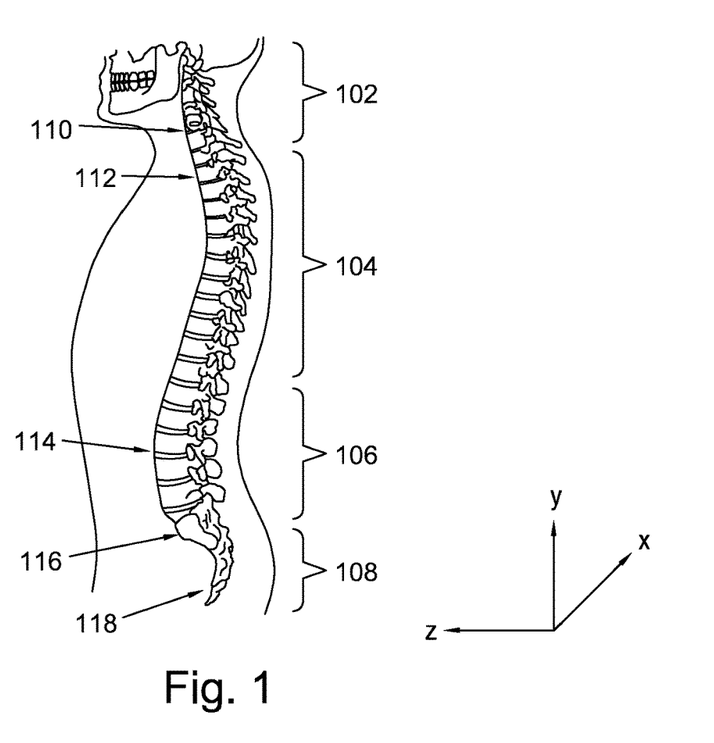
FIG. 1 shows a lateral (side) view of a normal vertebral column showing the various curved regions.

FIG. 1 shows a lateral view of the human vertebral column. The vertebral column has three major sections, each of which is differently curved. In a healthy patient, the cervical spine 102 is lordotic, the thoracic spine 104 is kyphotic, and the lumbar spine 106 is lordotic.

The vertebrae have different shapes and dimensions, particularly as one proceeds down the vertebral column. However, a vertebra typically comprises a cylindrical core known as the vertebral body having a smooth rounded surface facing the anterior (front) of the person's body. Each vertebra also typically has facets or structures projecting from the posterior of the vertebra. The pedicle is an example of a stem-like structure that projects from the posterior of the cylindrical body of a vertebra. There are two pedicles per vertebra and owing to their high bone density, the pedicles are typically used as anchoring locations for surgical screws, known as pedicle screws.

There are various abnormalities relating to curvature of the vertebral column. Vertebrae can become displaced in any of three dimensions with respect to each other. Correction may be necessary when displacement occurs outside of normal bounds and/or causes problems for the individual.

For example, abnormal displacement can occur in the anteroposterior direction. That is, the curves of FIG. 1 can become over-pronounced, potentially resulting in medical problems for the patient. Kyphosis is a condition that results when there is excessive (flexion) outward curvature of the thoracic curved region (i.e. towards the posterior) giving a humped-back profile. Lordosis occurs when there is excessive (extension) inward curvature (i.e. towards the anterior) of the lumbar or cervical curves.

Figure 2:
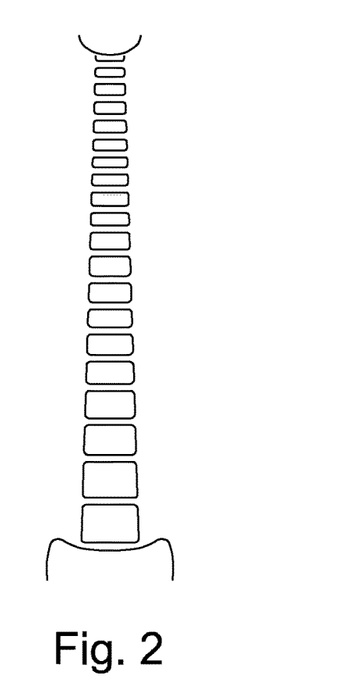
FIG. 2 shows an anteroposterior (AP, front) view of a normal vertebral column.
Figure 3:
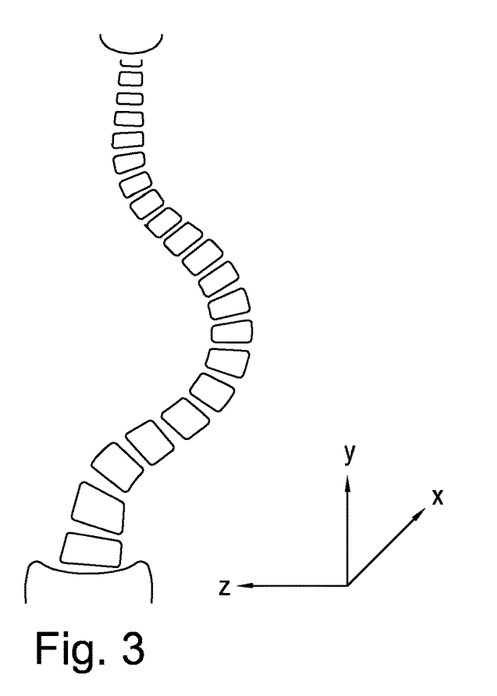
FIG. 3 shows an AP view of a vertebral column affected by scoliosis.

Curvature can also occur in the lateral (or 'side-to-side') direction. FIGS. 2 and 3 show anteroposterior (AP) views of different vertebral columns. Specifically, FIG. 2 shows a normal vertebral column, wherein the vertebrae are substantially aligned vertically when viewed from the anteroposterior direction (front). In contrast, FIG. 3 shows a vertebral column suffering from scoliosis (lateral curvature). It can be seen that the vertebrae in FIG. 3 are not aligned vertically, but are instead curved laterally (x-direction, as shown in the axes depicted in FIG. 3). In scoliosis, as well as lateral curvature there tends to be lordosis and rotation with the posterior elements directed towards the midline.

The most common type of scoliosis is idiopathic scoliosis, which affects many millions of people worldwide. A curvature of 10 degrees or more is present in 2 to 3% of the population. Surgery is usually recommended for curves which have a high likelihood of progression (i.e., greater than 45 to 50 degrees) and curves which are cosmetically unacceptable. Current surgical techniques most commonly use spinal implants and bone to fuse the spine in order to improve deformity and prevent curve progression. Surgery over a few hours attempts to correct a deformity which has been developing for months or years. Complete correction is rare because the bones deform in response to the abnormal forces and contractures occur because of the deformity.

The current "gold-standard" of scoliosis surgical techniques involves the implantation of hooks and screws to the spine to anchor long stabilizing rods. Problems with this approach include:
1. A large implant which runs the risk of infection.
2. Use of pedicle screws which may cause neurological damage, and may need to be removed.
3. The deformity will have been developing for many months or years. It is seldom possible to correct this deformity in the few hours of surgery.
4. Most current devices use spinal fusion. This prevents movement in the part of the spine which has been fixed. It also prevents most growth in that part of the spine.
5. Because the implants are stiff occasionally breakage of the implants can occur.

SUMMARY OF THE INVENTION

According to a first aspect of the invention there is provided device for adjusting (and preferably correcting) the curvature of a vertebral column, the device comprising a spring and at least three fixation members for attaching the spring to the vertebral column in at least three different locations.

In contrast to prior art devices, the devices described herein are flexible. We have determined that flexibility can be advantageous in a spinal correction device. As well as being able to correct part of a patient's deformity at the time of implantation, the flexible devices described herein are able to assist the spine's normal growth and remodelling process to further correct the deformity after implantation, while still permitting the spine to remain flexible.

A segment of the vertebral column may be defined between an adjacent pair of the locations. The vertebral column may comprise a plurality of such segments, each segment being defined between a pair of adjacent attachment locations (an attachment location may be shared between two adjacent segments).

The device may apply a first force to a first segment in a first direction and a second force to a second segment in a second direction. Such a device is thus able to apply different corrective forces to different segments of the spine, so allowing a three dimensional correction of the deformity. At least one of the forces may comprise multiple components.

At least one of the fixation members may comprise a tape or string. The tape or string may comprises a first end attached to the spring; and a second end attached to a vertebra of the vertebral column. The tape may be a flat tape so that it has a low profile when anterior to the vertebra.

The tape may be passed through a hole drilled in a body of the vertebra. The device may further comprise a hollow bicortical screw for fitting into the hole and for receiving the tape.

The tape may comprise a non-metallic material.

At least one of the fixation members may comprise a screw, and the spring may be attached to the screw. For example, the spring may be attached to a head of the screw located in a vertebra by passing around the head. If required, the spring may be separated from the metallic part of the screw by a non-metallic material.

The spring may be attached to a head of the screw located in a vertebra by passing a single loop of string around the spring and the head. The spring may be attached to a head of the screw located in a vertebra by passing a double loop of string around the spring and the head.

A configuration of the at least three attachment locations may be selected based on a predetermined curve analysis. The configuration may include, for example, the vertebra in which each attachment location is to be sited, the location site of each attachment location on the respective vertebra, the distance of the attachment locations from each other and/or the force/tension required between adjacent pairs of attachment locations.

The spring may wrap around the vertebral column.

A portion of the spring, and in particular a portion that wraps around an anterior of the vertebral column, may be replaced by a string or a (preferably flat) tape.

According to a second aspect of the invention there is provided a device for adjusting (and preferably correcting) the curvature of a vertebral column, the device comprising a plurality of springs, each spring for attaching to at least two locations of the vertebral column, and at least three fixation members for attaching the plurality of springs to the attachment locations of the vertebral column such that the plurality of springs are attached longitudinally along a length of the vertebral column. Preferably two adjacent springs are attached to one common attachment location.

The device described above in the second aspect of the invention may include any of the features described above with respect to the first aspect of the invention. For example, the fixation members may be as described above. A portion of one or more of the springs may be replaced with a string or a tape, as discussed above. Alternatively or additionally, one or more of the springs may be replaced with a string or tape.

According to a third aspect of the invention, there is provided a kit for adjusting the curvature of a vertebral column, the kit comprising a plurality of devices in accordance with any preceding claim, each device having a spring having a different tension. Such a kit allows a clinician to select an appropriately tensioned device for implantation.

The kit may further comprise a string or tape for attaching at least one of the springs to a location of the vertebral column; a hollow bicortical screw for attaching the tape to the location; and an instrument for threading the tape through the hollow bicortical screw.

According to a further aspect of the invention, a method of adjusting the curvature of a vertebral column comprises attaching a spring to a plurality of locations of the vertebral column, the spring being tensioned to apply a plurality of forces for adjusting the vertebral column.

The method may comprise attaching the spring to the vertebral column, and then tensioning the spring. Alternatively, the method may comprise tensioning the spring and then attaching the spring to the vertebral column.

The method may further comprise adjusting the tension of the attached spring.

The spring may be attached to each location using a fixation member, such as a screw. The method may comprise attaching the spring to each location by looping the spring around the screw and/or securing the spring to the screw using a loop of string. Adjusting the tension of the attached spring may comprise moving the looped spring and/or moving the loop of string along spring relative to a screw until a desired tension is reached.

As discussed above, we provide herein a flexible device which may comprise screws, bands and springs. The device can be attached to the spine by an anterior approach. The device is able to correct a spinal deformity in three dimensions.

A device of the type described herein may provide some or all of the following advantages:

1. The device may provide forces on the spine.
2. The device may be positioned so that the forces it applies will tend to correct the deformity.
3. The forces applied by the device may provide some immediate correction of the deformity at the time of surgery.
4. The forces applied by the device may progressively correct the deformity with time.
5. By applying the device anteriorly in tension the device may apply compression to the anterior spine and correct the lordotic deformity typical of scoliosis.
6. By applying the device obliquely the device may derotate the typical rotational deformity seen in scoliosis.
7. Because the device applies force over time the device may indirectly improve the rib hump.
8. Because fusion is not necessarily used the device may allow movement of the spine to continue in the instrumented area,

BRIEF DESCRIPTION OF DRAWINGS

Embodiments of the invention will now be described, by way of example only, with reference to the accompanying drawings, in which.

DETAILED DESCRIPTION

The Figures show a device for adjusting the curvature of a vertebral column. The device comprises a spring (or springs) and at least three fixation members for attaching the spring to the vertebral column in at least three different locations.

By attaching the spring at three locations, at least two segments of the vertebral column are defined. Specifically, a segment is defined between each pair of adjacent locations.

If there is a first, second and third location, then a first segment is defined between the first and second locations, while a second segment is defined between the second and third locations.

The spring is capable of applying a first force to a first segment and a second force to a second segment, wherein the direction and intensity of the first force may be different to the direction and intensity of the second force. This allows one spring to adjust for a spine having different intersegmental deformities. The configuration (e.g. siting) of the locations will determine a direction of the force applied by the spring to each of the segments of the vertebral column. That is, the direction of the force applied by the spring to a given segment of vertebral column will depend on the selection of the attachment locations defining that segment.

The direction of the force applied to any particular segment can have multiple components. In other words, a spring segment may simultaneously apply a force in a lateral (x) direction, a longitudinal (y) direction and an anteroposterior (z) direction. By configuring the locations of attachment, the spring can be bent or wrapped around the spine, which enables complex forces, including rotation, to be applied to each segment of the vertebral column.

During the attachment process the spring can be tensioned so it corrects the flexible part of the deformity and additional tension will be applied which will cause progressive correction after the operation. Each segment of the spring may have a different tension. Such a device is able to correct the flexible part of a spinal deformity at the time of the operation and afterwards allows the normal growth and remodelling processes to correct the remaining deformity with time.

In an alternative embodiment, a device for adjusting the curvature of a vertebral column can be provided which comprises a plurality of springs, where each spring is attached to at least two locations of the vertebral column. The springs may be attached at discrete locations longitudinally along the spine, or some or all adjacent springs may share a common attachment location. For example, where the plurality of springs are attached to at least three locations of the vertebral column such that the plurality of springs are attached longitudinally along a length of the vertebral column, at least two adjacent springs might be attached to at least one common location.

Therefore, rather than use a single spring to apply a different force to different segments of the vertebral column, a separate spring can be used for some or each of the segments. In such an arrangement, some of the locations of attachment may be the same for adjacent springs. For example, a first spring is attached at one end to a first vertebra and, at another end, to a second vertebra that is located beneath the first vertebra. A second spring is attached at one end to the second vertebra and, at the other end, to a third vertebra that is located beneath the second vertebra. In such a configuration, the first and second springs are attached longitudinally along a length of vertebral column and the first and second springs have at least one common location, i.e. the second vertebra.

Figure 4:
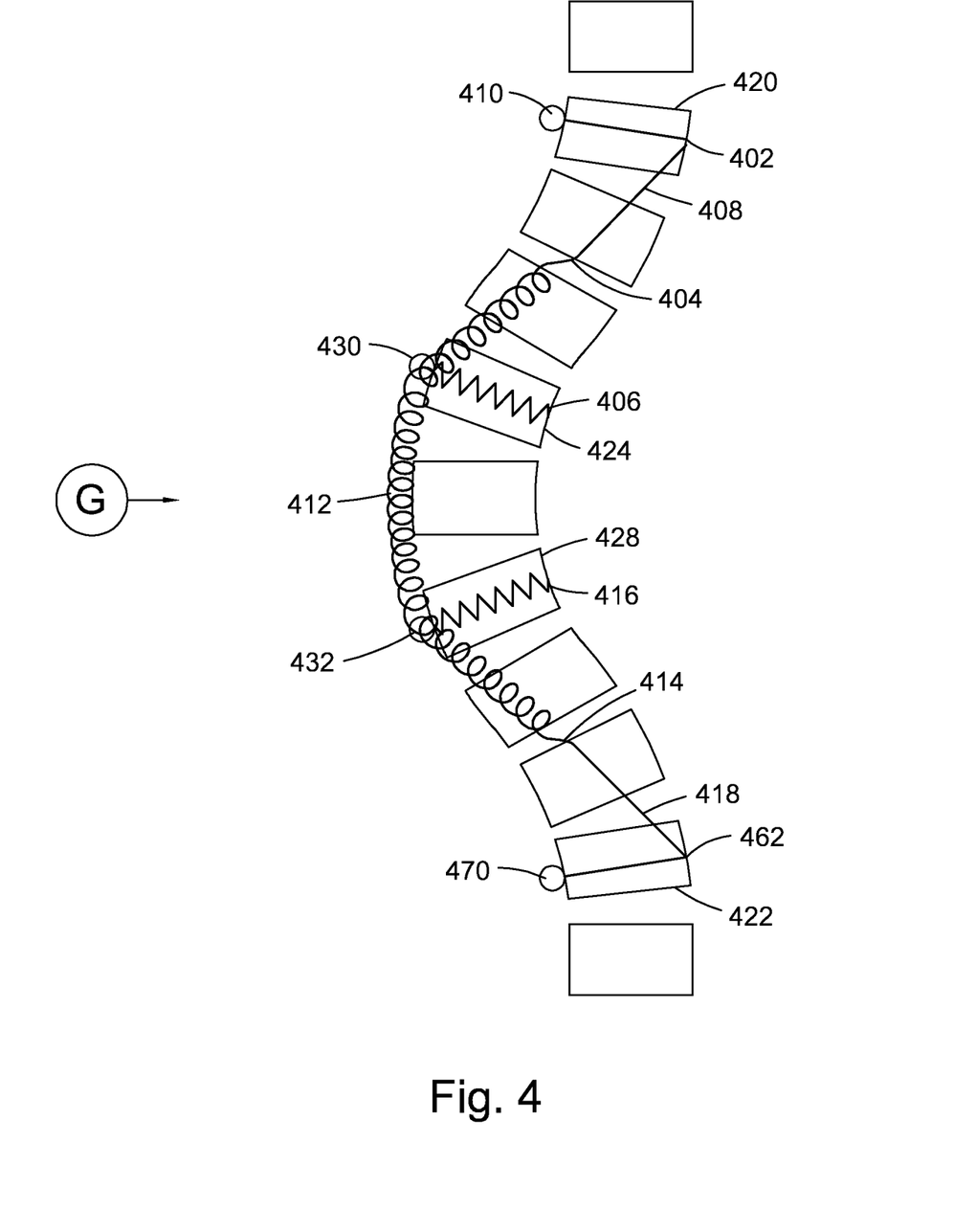
FIG. 4 shows a device for adjusting the curvature of the vertebral column.

FIG. 4 shows an anteroposterior (AP) view of a vertebral column including a device according to one embodiment. In FIG. 4, the overall deformity of the vertebral column consists of lordosis, lateral curvature and rotation. At the apex of the curve the intervertebral deformity is predominantly lateral curvature and lordosis. At the mid-point between the main curve and the compensatory curve the intervertebral deformity is predominantly rotation and lordosis. At other points on the curve the intervertebral deformity is a combination of all three deformities.

As discussed above, an intervertebral deformity can be corrected by applying a force, for example with a spring, between the adjacent vertebrae. Intervertebral deformities are combined deformities, and so if there are similar intervertebral deformities at a few adjacent levels (i.e. adjacent vertebra), then instead of attaching the spring to every vertebrae, each segment of spring might span a few vertebra.

Springs can be in tension or compression. Longitudinal tension springs at the front of the spine, or longitudinal compression springs at the back can address lordosis. The example shown in FIG. 4 uses an anterior approach to the spine and so uses tension springs. Lateral curvature is thus addressed with longitudinal springs on the outside of the curve, and rotational deformities are addressed by circumferential springs parallel to the disk.

Figure 6A:
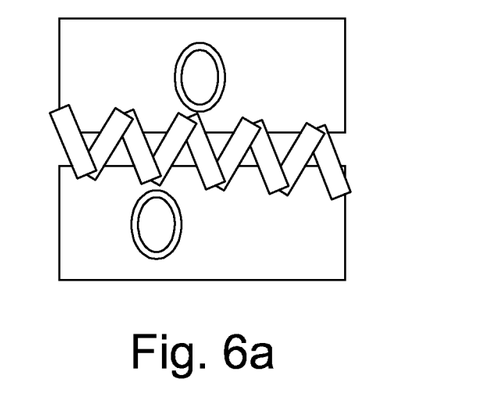
FIG. 6a shows a spring tensioned to correct for a rotational deformity.
Figure 6B:
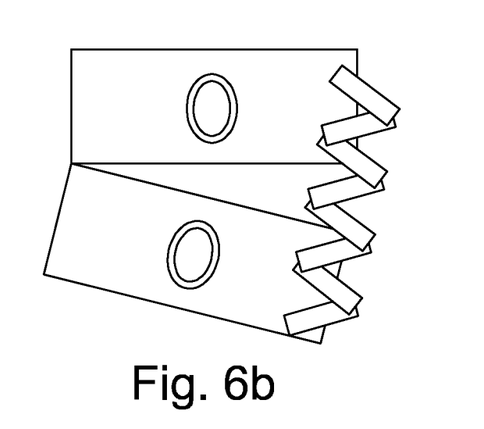
FIG. 6b shows a spring tensioned to correct for a lateral deformity.
Figure 6C:
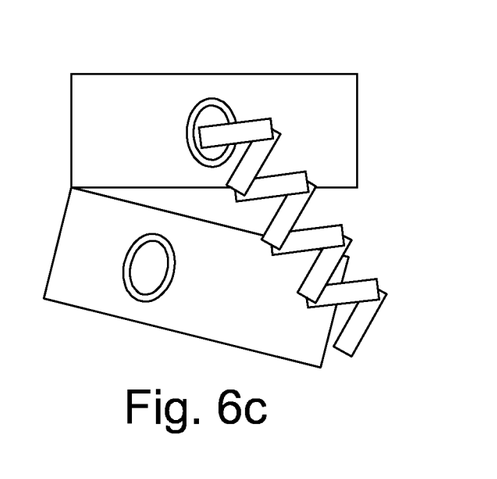
FIG. 6c shows a spring tensioned to correct for a combination of deformities in three dimensions.

FIGS. 6a to 6c show examples of different directions in which forces can be applied by varying the attachment locations of the spring. The ellipse on each vertebra represents the posterior element (the vertebral spine) of that vertebra and thus demonstrates the rotation of the vertebra. The more off-centre the ellipse is shown on the vertebra, means the greater the angle of rotation (i.e. rotational deformity) of the vertebra.

FIGS. 6a to 6c show how the springs have to be positioned at different locations to correct for different intersegmental deformities. Or put another way, the configuration of the spring in terms of its attachment locations to the vertebra to ensure the direction of the force applied.

More specifically, FIG. 6a shows a rotational deformity, in which it can be seen from the mal-aligned ellipses that the posterior elements of one of the vertebra has rotated about a central vertical axis. Such a deformity can be corrected by a horizontal spring that is attached to extend circumferentially and is tensioned to counter-rotate the mal-aligned vertebra. The force applied thus extends generally laterally.

FIG. 6b shows a lateral curvature of the vertebral column. That is, the vertebra are aligned in an axial sense (ellipses are substantially aligned and there is no rotation), but the bottom vertebra has titled laterally out of the normal limits. Such a lateral deformity is corrected by a spring being attached such that it is tensioned in a vertical direction on the apex of the convexity. Similarly, a lordosis deformity may be corrected by a spring being attached such that it is tensioned in a vertical direction on anterior of the spine. Thus the force applied by such a spring is generally exerted longitudinally.

FIG. 6c shows a combination of axial and lateral mal-alignment, which can be corrected by a spring that is tensioned obliquely so as to simultaneously provide longitudinal, axial and torsional forces to correct for the mal-aligned vertebra in all three dimensions.

Referring again to the example of FIG. 4, an example pair of adjacent attachment locations is shown at screw heads 430 and 432 of vertebra 424 and 428 respectively, which define a segment of the vertebral column therebetween. The attachment of the spring to the screw heads at least partially isolates the spring in that segment from the remainder of the spring. Thus, it is the attachment locations of the spring which cause a plurality of forces to be directed through the spine. Further attachment locations at bores 402 and 462 define two further spinal segments, an upper segment between locations 402 and 430 and a lower segment between locations 432 and 462.

The spring between screw heads 430 and 432 being on the outside of the curve will correct the lateral curvature at this level. Similarly the spring between 430 and 402 and between 432 and 462 being oblique will correct the rotational deformities at these levels. Therefore the combined forces have the overall effect of pulling the apex of the deformity in the direction of arrow G and derotating the deformity (to the extent that it is flexible in that direction). This will at least partially correct the deformity. In addition the forces also affect the growth between the attachment locations, so that as the spine grows it resumes a more natural curve. Both of these processes act to correct the deformity of the spine. The mechanism by which growth is altered depends on relative contributions of the various intervertebral deformity. With lateral curvature growth will either or both be increased on the concavity and decreased on the convexity. With lordosis growth will either or both be increased at the back and decreased at the front the convexity. With rotation there will be spiral growth.

It should be appreciated that arrow G only indicates a general direction of the force in the apex segment region, which acts to adjust or counter the curvature of the apex. In other words, the spring will cause a plurality of forces to be distributed over the length of the segment depending on how the spring is applied. The general direction of the force (or forces) applied to one segment (defined by the attachment locations of the spring) is capable of being quite different from the general direction of the force (or forces) applied to another segment, and is therefore different to the overall force applied to the spine.

The attachment locations of the spring allow a plurality of forces to be applied simultaneously in different directions depending on how the spring is applied. If required, the spring can be bent or wrapped around the spine to provide forces in three-dimensions. Therefore, by connecting the spring to carefully selected attachment locations, it is possible to correct for different elements of a spinal deformity simultaneously.

FIG. 4 shows a scoliotic spine in which the vertebral column comprises a plurality of vertebrae in a laterally curved arrangement, and a single spring 412 attached to the vertebral column in a configuration designed to adjust, and preferably correct, the curve.

Specifically, the spring 412 is connected to tapes 408 and 418 at points 404 and 414 respectively. In turn, the tapes are attached to the vertebra 420 and 422 respectively. In the region of the apex of the curve, the spring is located on the lateral side of the curve by attaching it to heads 430 and 432 of bicortical screws 406 and 416 respectively. The bicortical screws are located in the vertebrae 424 and 428 respectively. The spring 412 is in tension and the individual segments sum together to apply a general force in the direction of arrow G to counteract or correct the lateral curvature at the apex, and a force to derotate the deformity.

The spring 412 with tapes 408 and 418 is configured to wrap around the front of the spine. Specifically, the upper part of the spring 412 that is connected to tape 408, attaches to the location point 402 of vertebra 420. The lower part of the spring 412 that is connected to tape 418, attaches to the location point 462 of vertebra 422.

It can be advantageous to use a tape or string for the portion of the device that wraps around the front of the spine, since a spring could pose a risk to the great vessels at the front of the spine. Moreover, a tape that is flat can be better able to distribute the forces applied to the front of the spine and the great vessels thereabouts. It will be appreciated that there are various ways that such a tape or string would be attached to the end of the spring. For example the tape/string could be to weaved into the spring or pass through a loop in the end of the spring. If passed through a loop in the spring either a loop could be formed in the end of the tape or string to achieve this or the two ends of the string and tape could be kept separate which may facilitate final fixation as the ends can be tied together.

In addition to the apex region of the spring being under tension, these upper and lower parts of the spring and tape are also under tension. Whereas the apex region of the spring is (in this example) used to correct the intersegmental lateral mal-alignment, the upper and lower parts of the spring and tape are used to correct the intersegmental rotation.

To achieve attachment at locations 402, 462 a hole is drilled through the vertebrae 420, 422 and the tapes 408, 418 are passed through the hole. After tension is applied to the tape it is tied off or locked with a fixation device at points 410, 470.

To prevent the tape cutting into the bone at locations 402 and 406 in which the hole has been drilled, a hollow bicortical screw (not shown) could be passed through the vertebra 420 from point 402 to point 410. The tape is then passed through the hollow bicortical screw to prevent the tape cutting into the bone.

It may be desirable when implanting the device to approach the spine from the side, in the direction of arrow G, but threading the tape through at location 402 will require a special instrument to be passed through the vertebrae from locations 410 to 402 to retrieve the end of the tape. The instrument could have a pre-bent piece of wire passed through a tube. After the tube is placed through the hole in the bone, the wire is advanced and because of the bend it will go anteriorly and can be used to retrieve the end of the tape or string. This may be facilitated by having a loop in the end of the wire through which a thin string attached to the end of the tape or string can be passed.

In summary, to achieve attachment to the far side of the spine, a string or tape (connected to the spring) could pass through a hole in the spine and be fixed on the near side of the spine. If required, the string or tape could pass through a hollow bicortical screw located within a vertebra.

As mentioned briefly above, various types of connections between the tapes 408, 418 and the spring 412 at points 404, 414 could be used, the simplest being a wire loop made from the end of the spring through which the tape is passed. Both ends of the tape are then passed through the vertebra at point 402 to point 410 and are tied over or locked with a fixation device at point 410.

Various types of connections can also be made between the spring 412 and the heads 430, 432 of the bicortical screws 406, 416. The simplest would be to hook the spring around the top of the screw. This would result in metal rubbing on metal. To prevent this a piece of material, for example polyethylene could be placed between the metal of the screw and the spring. This could be shaped to form a smooth curve in the spring, rather than a sudden bend. In addition its surface could be made to fit the spring and thus stop it slipping.

Figure 5A:
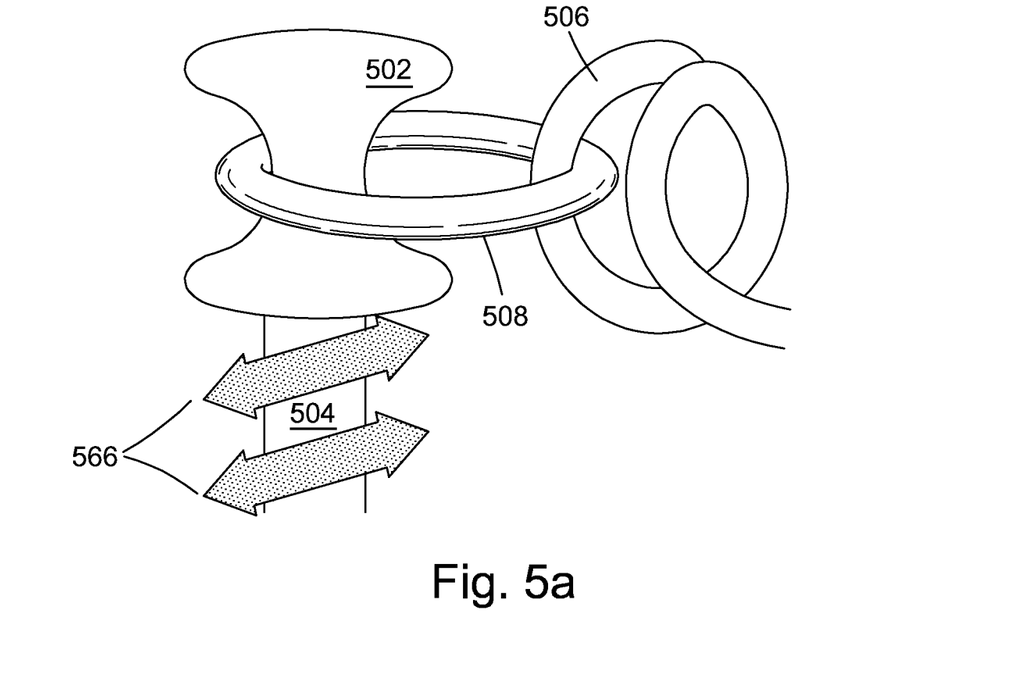
FIG. 5a shows a single loop attachment to a vertebral screw.
Figure 5B:
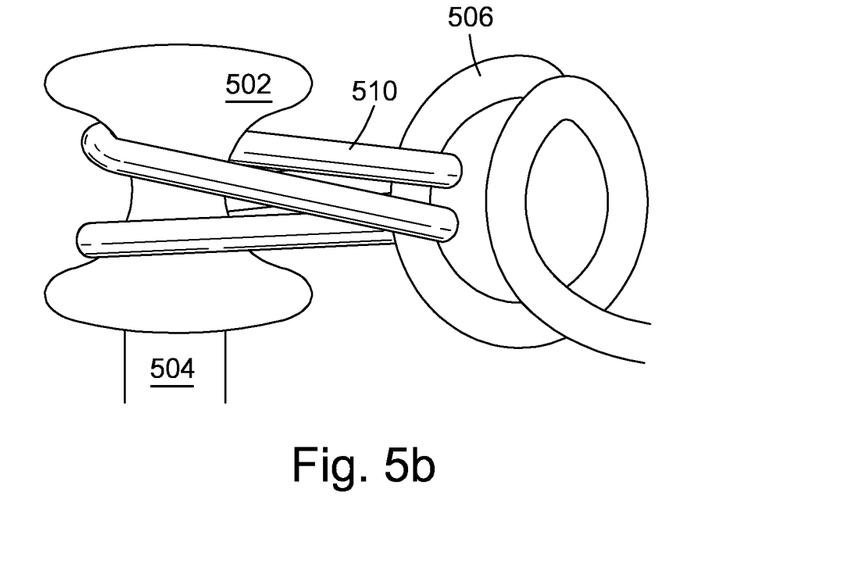
FIG. 5b shows a double loop attachment to a vertebral screw.

FIG. 5 shows two further examples for connecting the spring with bicortical screws using a loop of string. This advantageously avoids rubbing metal on metal. The string loop goes around the spring and around a bollard on the top of the screw. As the loop will pass around a single wire coil of the spring it will not slip along the spring.

FIG. 5a shows that a single loop of string 508 is able to pass around a head (or bollard) 502 of the screw 504 (having thread 566) and through a wire loop 506 of the spring.

FIG. 5b shows a double loop of string 510 being used for the connection. Thus, either a single loop 508 or a double 510 loop could be used.

A single loop would have to be passed over the spring before it is inserted. A double loop could be positioned after spring implantation. The double loop 510 would go around the bollard 502, then around the spring wire 506, then back around the bollard 502 as shown in FIG. 5b.

As discussed above, we have devised implantable devices for straightening, or correcting, the vertebral column. The devices each incorporate a spring, or springs, held in place at various selected locations along the vertebral column. The decision about where to site the various attachment points (i.e. how to distribute the various forces over the various segments of the spine) is based on a curve analysis. In particular, software or an algorithm can be used to analyze at what precise locations the spring should be attached, or the amount of tension to be applied, to produce the required corrective forces depending on a particular patient's deformities. A surgeon can therefore simply select a spring with a specific tensile force and connect it to the locations calculated.

Figure 7:
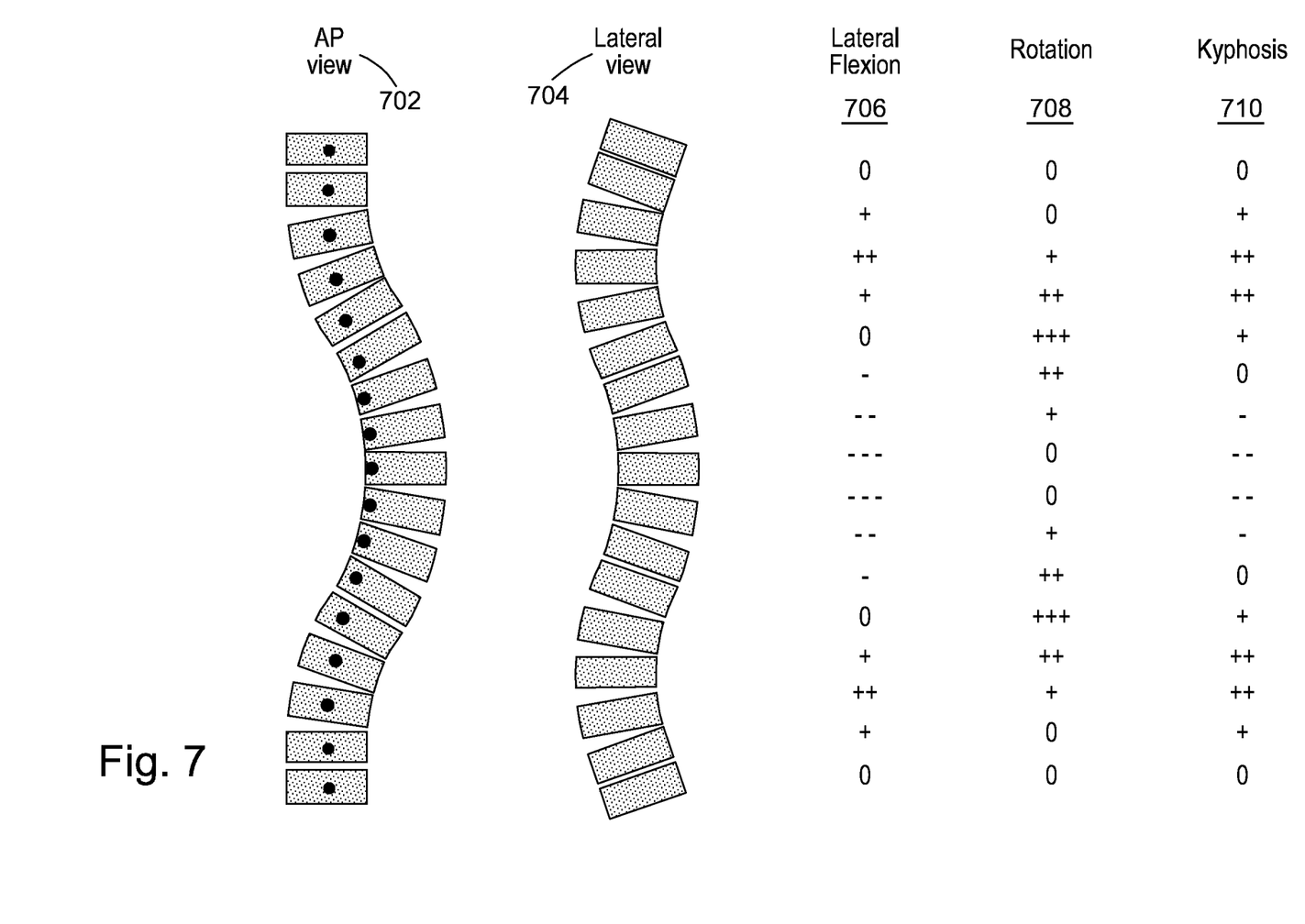
FIG. 7 shows an intervertebral deformity curve analysis.
Figure 8:
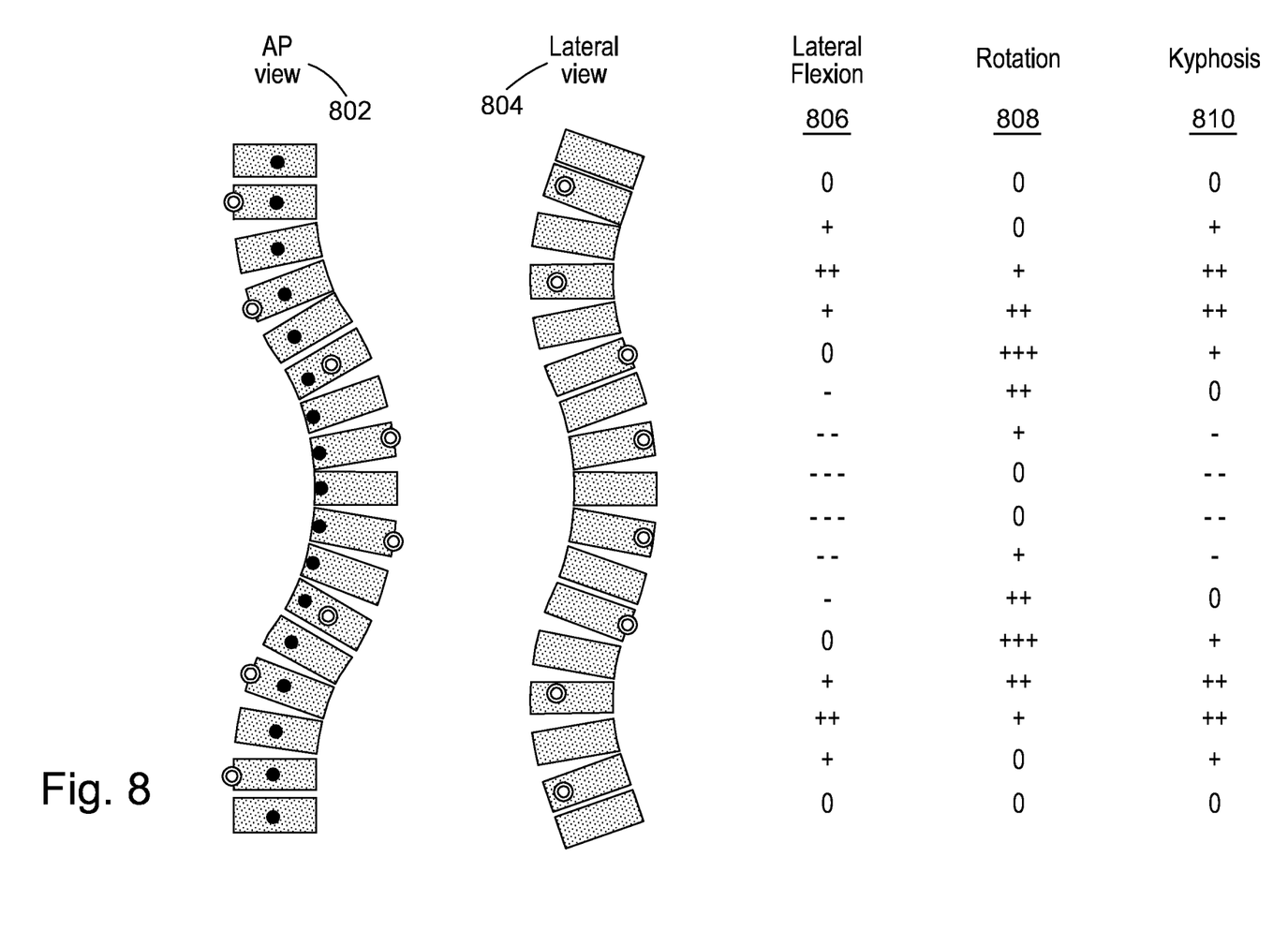
FIG. 8 shows spinal attachment locations in AP and lateral views based on the curve analysis of FIG. 7.
Figure 9:
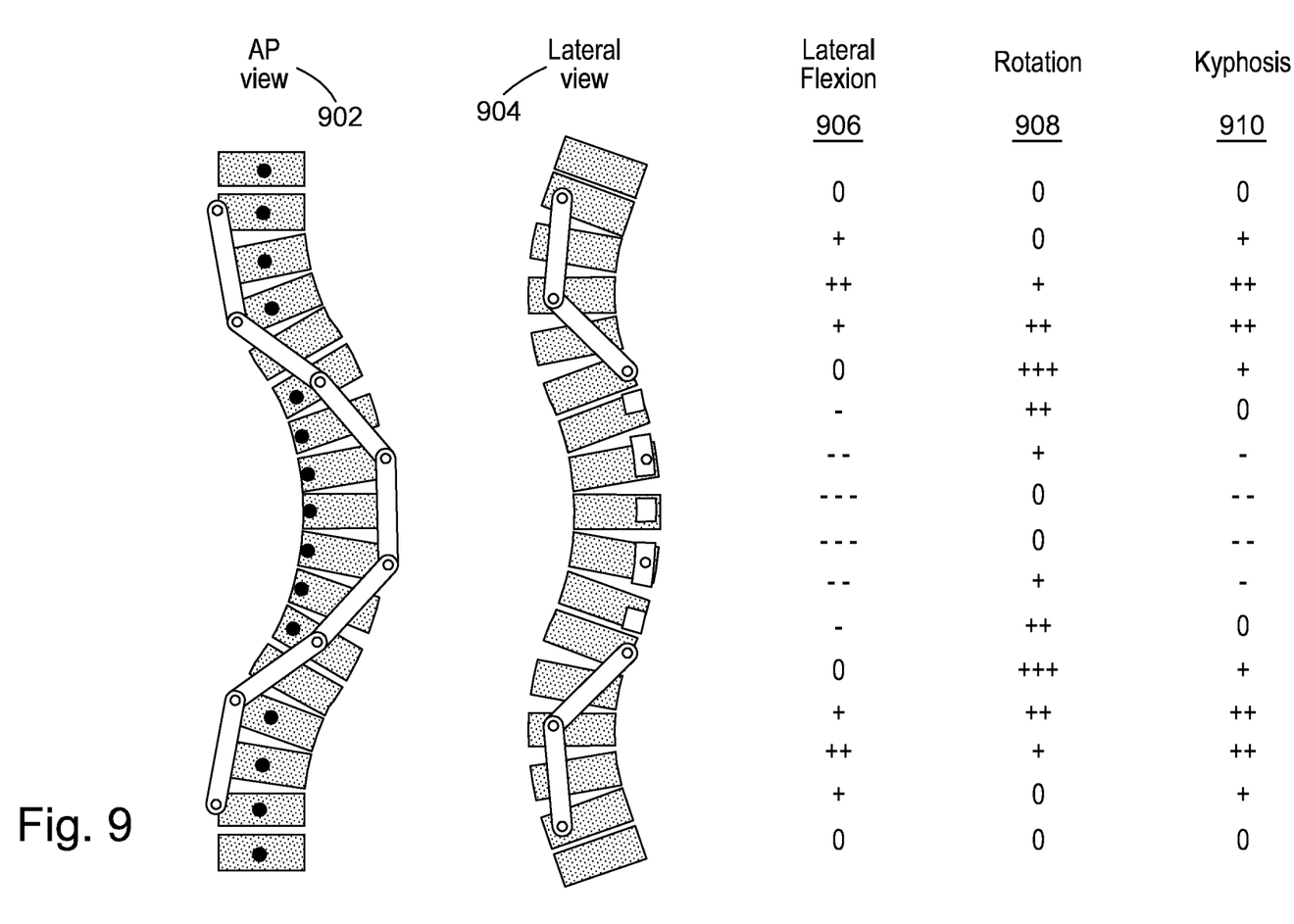
FIG. 9 shows a device for adjusting the curvature of a vertebral column attached to a vertebral column based on the curve analysis of FIG. 7.

FIGS. 7-9 show an example of a curve analysis for a vertebral column requiring corrective alignment. Each of these Figures shows both an AP view 702, 802, 902 and a lateral view 704, 804, 904 of the curved vertebral column. The solid circles in the AP view represent the rotation of the posterior elements (vertebral spine) in the AP view (i.e. the ellipses of FIG. 6).

Alongside these curves are three analytical columns, each column showing an amount of the intervertebral deformity in a particular direction. That is, the first analytical column 706, 806, 906 shows the amount of lateral flexion. The second analytical column 708, 808, 908 shows the amount of rotation. The third analytic column 710, 810, 910 shows the amount of kyphosis/lordosis. That is, kyphosis is indicated with a "+", whereas lordosis is indicated by "−".

More generally, the "+" symbol indicates a deformity (i.e. excessive curvature) in one direction, while the "−" symbol indicates a deformity in the other direction. The more symbols that are stacked together the greater the intervertebral deformity. For example, "+" indicates slight deformity, "++" indicates significant deformity, "+++" indicates a very significant deformity, etc. The symbol "0" indicates that there is no deformity of that type to correct and the intervertebral alignment is normal.

Following a curve analysis, in which the deformities have been imaged and measured (as shown by the three columns in FIG. 7), a configuration for attaching the spring to locations of the vertebral column to induce the required corrective forces is calculated. FIG. 8 shows the various attachment locations determined for this particular vertebral column, indicated by hollow circle symbols, in both the AP view 802 and the lateral view 804.

As can be seen there are eight attachment locations in this example. FIG. 9 shows the spring, or springs, being attached to the plurality of selected attachment locations.

As suggested above, a single long spring can be implanted by the surgeon at the plurality of pre-selected locations, which allows for a multi-dimensional deformation correction using a single continuous spring. Alternatively, a plurality of springs can be implanted at adjacent calculated locations, which also allows for a multi-dimensional deformation correction, but using a plurality of individual springs aligned end to end. In the clinical situation the surgeon may feel that the springs need not be extended into the compensatory curves at the top and bottom of the deformity. In addition the surgeon may choose to use a tape or spring instead of a spring in the region of the great vessels.

There are a number of methods by which the springs could be applied and tensioned. They could for example be attached at their ends and pulled around the front of the spine and then attached to the apical screws. Alternatively they could be attached to the apical screws then tensioned at their end attachments. Any tension could be applied to the springs. Possibly a multiple of the amount of tension that would correct the correctable portion of the deformity would be applied. This multiple would be determined by clinical practice but might be about twice.

The attachable-spring devices described herein are flexible. They apply a continuous load to the spine which corrects the correctable part of the deformity and also improves the mechanical environment of the spine. This allows the normal growth and remodelling processes to correct the non-correctable parts of the deformity. It also allows the spine to remain flexible and to grow.

Using the devices described herein spinal deformities can be corrected at an intersegmental level. The overall deformity consists of the additive effect of all the deformities between adjacent vertebrae (the intersegmental deformities). If each of these intersegmental deformities are corrected the overall deformity will be corrected.

The device is customisable in terms of length of the spring, stiffness of spring, amount of spring stretch, number and position of bone screw fixation devices—all of which can be tailored to suit patients' specific requirements. Therefore, the device is highly customisable to treat patients' unique anatomical curvature. It is likely that the forces applied by the spring will be in the 10 to 1000 Newton range, perhaps in the range 20 to 200 N.

The flexibility and relatively low loads engendered by the devices described herein mean the devices are harder to break as compared with other more rigid fusion devices. No bone grafts or spinal fusion are necessary with the device according to the described embodiments. The device is more easily implanted and removed, as compared with other existing anterior fixation devices, and could be inserted thorascopically. The device can be produced relatively cheaply using medical-grade metallic alloys and polymers or other suitable materials. No housing is required for the spring.

If the apical portion of the curve is stiff or fused an additional embodiment could be that the apical segment is corrected by removal of the disc and possibly bone, and then fused. A spring device as described herein could then be used above and below the fused segment. The springs could possibly be attached to the fixation device for the fusion.

As the surgery required to implant the present devices can be much less invasive than prior methods, use of such devices will be less risky and therefore appropriate not only for patients with rapidly progressing deformities, who will end up with major cosmetic abnormalities, but also for those patients with less severe curves and moderate cosmetic abnormalities.

If required, rather than supplying the surgeon with a bespoke spring device, the surgeon may be provided with a kit of parts for implanting the spring device, the kit comprising a plurality of device components allowing the surgeon to make a choice of which to use based on the curve analysis and measurements performed on the individual. For example, the kit may include springs that have different tensions and lengths.

It will be understood that alterations and modifications can be made to the above described embodiments without departing from the scope of the invention as defined herein.

The invention claimed is:

1. A system for correction of a vertebral column having an abnormal curvature, the curvature having a first end, a second end and an apex between the first and second ends, the system comprising:
   a fixation member configured to attach to a vertebra of the vertebral column on a first side of the vertebral column adjacent the apex of the abnormal curvature;
   a first hollow bicortical screw having a first screw head and configured to provide a bore through a second vertebra of the vertebral column adjacent the first end of the abnormal curvature;
   a second hollow bicortical screw having a second screw head and configured to provide a bore through a third vertebra of the vertebral column adjacent the second end of the abnormal curvature; and
   a flexible device having a first device end and a second device end;
   wherein the flexible device is configured to thread through the first hollow bicortical screw between the first side of the vertebral column and a second side of the vertebral column, the first device end configured to be fixed to the first screw head on the first side of the vertebral column;
   wherein the flexible device is configured to thread through the second hollow bicortical screw between the first side of the vertebral column and the second side of the vertebral column, the second device end configured to be fixed to the second screw head on the first side of the vertebral column; and
   wherein the flexible device is configured to loop around the fixation member and apply a first force to the apex to reduce the abnormal curvature.

2. A kit for correction of a vertebral column having an abnormal curvature, the kit comprising the system of claim 1, and an instrument for threading the flexible device through the first and second hollow bicortical screws.

3. The kit of claim 2, wherein the flexible device is or comprises a spring.

4. The kit of claim 2, wherein a first segment of the vertebral column is defined between the first hollow bicortical screw and the fixation member, and wherein the flexible device is configured to apply a second force to the first fixation element in a first direction and a third force to the fixation member in a second direction.

5. The kit of claim 4, wherein a second segment of the vertebral column is defined between the second hollow bicortical screw and the fixation member, and the flexible device is configured such that forces applied within the first segment are different from forces applied within the second segment.

6. The kit of claim 5, wherein the directions of the second and third forces are selected such that the flexible device is operable to apply a rotation within at least one of the first and second segments.

7. The kit of claim 2, wherein a configuration of the locations of the first hollow bicortical screw, second hollow bicortical screw and the fixation member is selected based on a predetermined curve analysis.

8. The system of claim 1, wherein the flexible device is or comprises a spring.

9. The system of claim 1, wherein a first segment of the vertebral column is defined between the first hollow bicortical screw and the fixation member, and wherein the flexible device is configured to apply a second force to the first fixation element in a first direction and a third force to the fixation member in a second direction.

10. The system of claim 9, wherein a second segment of the vertebral column is defined between the second hollow bicortical screw and the fixation member, and the flexible device is configured such that forces applied within the first segment are different from forces applied within the second segment.

11. The system of claim 10, wherein the directions of the second and third forces are selected such that the flexible device is operable to apply a rotation within at least one of the first and second segments.

12. The system of claim 1, wherein a configuration of the locations of the first hollow bicortical screw, second hollow bicortical screw and the fixation member is selected based on a predetermined curve analysis.

* * * * *